Sept. 4, 1956 E. S. BOERNER Plant Pat. 1,512
ROSE PLANT
Filed Oct. 27, 1955
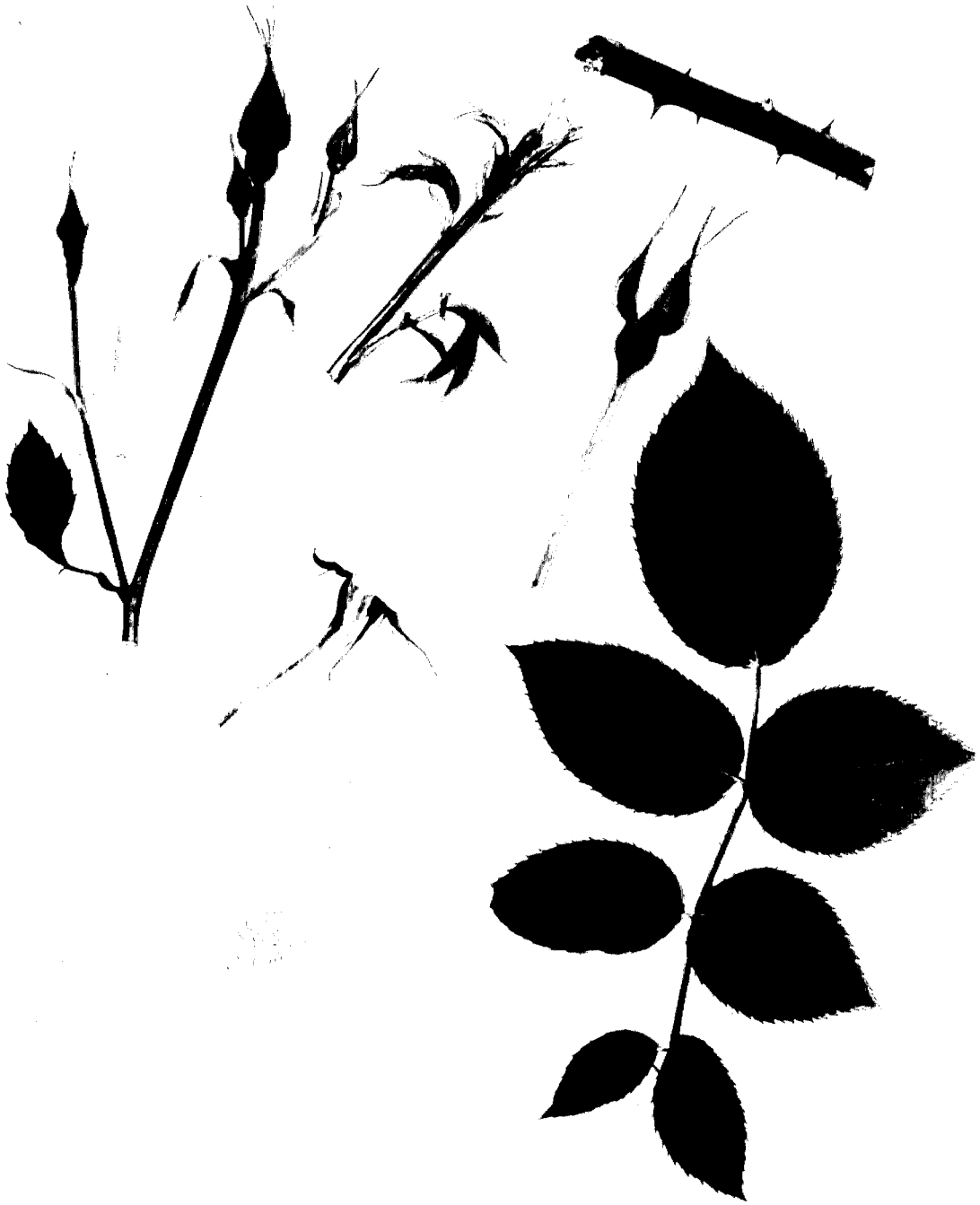
Inventor.
E. S. Boerner
By: Robb & Robb
Attorneys.

United States Patent Office

Plant Pat. 1,512
Patented Sept. 4, 1956

1,512

ROSE PLANT

Eugene S. Boerner, Newark, N. Y., assignor to Jackson & Perkins Company, Newark, N. Y., a corporation of New York Application October 27, 1955, Serial No. 543,291

1 Claim. (Cl. 47—61)

The present invention relates to a new and distinct variety of rose plant of the large-flowered polyantha class, which was originated by me by crossing the variety "Diamond Jubilee" (Plant Patent No. 824) with the variety "Yellow Sweetheart" (Plant Patent No. 1011).

The primary objective of this breeding was to produce a new rose variety of the Yellow floribunda class, the flowers of which have a stiffer neck and firmer petals than the flowers of the parent variety "Yellow Sweetheart." This objective was fully achieved, as evidenced by the following novel and distinctive features which are outstanding in and particularly differentiate the new variety from its parents, as well as from all other varieties of which I am aware:

(1) The large, firm and stiff flower petals which are very resistant to rain;

(2) The strong flowering stem and stiff neck, resulting in always causing the flowers to face upward; and (3) The distinctive Buff Yellow, lightly overcast with Baryta Yellow, general color tonality of the flowers which lightens, but does not fade completely even in the final stage of maturity.

Asexual reproduction of my new variety by budding, as performed at Newark, New York, and also at Pleasanton, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Diamond Jubilee."
*Pollen parent.*—"Yellow Sweetheart."
Classification:
*Botanic.*—Large-flowered polyantha.
*Commercial.*—Floribunda.

FLOWER (Observations made from specimens grown outdoors at Newark, New York, in the early part of the month of July and in the early afternoon.)

Blooming habit: Recurrent—continuous.
Bud:
*Size.*—Medium.
*Form.*—Ovoid; is not affected by wet or hot weather.
*Color.*—When sepals first divide—Pinard Yellow, Plate 4. When petals begin to unfurl—Light Orange Yellow, Plate 3, lightly overcast with Capucine Orange, Plate 3. When half-blown: inside of petals—Pale Orange Yellow, Plate 3, lightly overcast with Maize Yellow, Plate 4, and with edges of petals lightly overcast with Shrimp Pink, Plate 1; reverse of petals—Apricot Yellow, Plate 4, with upper half of petal lightly overcast with Baryta Yellow, Plate 4.
*Sepals.*—Slightly branched; curl back when petals begin to unfurl. Color: inside—Kildare Green, Plate 31; outside—Cress Green, Plate 31.
*Calyx.*—Color—Cress Green, Plate 31. Shape—pear. Size—small. Aspect—smooth. Odor when rubbed—none.
*Peduncle.* — Length — short. Aspect — Rough. Strength—stiff; slender. Color—Light Bice Green, Plate 17.
*Opening.*—Opens up well; is not affected by adverse weather conditions.

Bloom:
*Size.*—Large. Average size when fully expanded—4½ inches.
*Borne.*—Sometimes singly and sometimes several together.
*Stems.*—Medium length; strong.
*Form (when first open).*—Cupped. Permanence—retains its form to the end; outer petals curl back.
*Petalage.*—Double (full but open center). Number of petals under normal conditions—from 35 to 40.
*Color.*—Center of flower—Empire Yellow, Plate 32, lightly overcast with Orange-Buff, Plate 3. Outer petals—Maize Yellow, Plate 3, with edges of petals lightly overcast with Capucine Buff, Plate 3. Base of petals (aiglet)—Strontian Yellow, Plate 16. Inside of petals—Buff Yellow, Plate 4, lightly overcast with Baryta Yellow, Plate 4. Reverse of petals—Maize Yellow, Plate 3, lightly overcast with Pale Flesh Color, Plate 14. General tonality from a distance—Buff Yellow, Plate 4, lightly overcast with Baryta Yellow, Plate 4.
*Discoloration.*—General tonality at end of first day—Buff Yellow, Plate 4. Second day—Buff Yellow, Plate 4, lightly overcast with Baryta Yellow, Plate 4. Third day—Buff Yellow, Plate 4, overcast with Baryta Yellow, Plate 4.
Petals:
*Texture.*—Thick; is not affected by wet or hot weather.
*Appearance.*—Inside—satiny; outside—shiny.
*Form.*—Oval; slightly notched.
*Arrangement.*—Irregular.
*Petaloids in center.*—Few; small.
*Persistence.*—Drop off cleanly.
*Fragrance.*—Strong. Nature—tea; very sweet.
*Lasting quality.*—On the plant—very long. As cut flower—very long.

GENITAL ORGANS

Stamens, anthers: Medium size; many; regularly arranged around styles. Color—Pinard Yellow, Plate 4.
Stamens, filaments (threads): Medium length. Color—Grenadine Pink, Plate 2.
Pollen: Color—Baryta Yellow, Plate 4.
Styles: Bunched; uneven length; short; thin.
Stigmas: Color—Sulphur Yellow, Plate 5.
Ovaries: All enclosed in calyx.
Hips: None.
Seeds: None.

PLANT

Form: Bush.
Growth: Vigorous.
Foliage: 5 to 7 leaflets.
*Size.*—Medium.
*Quantity.*—Normal.

*Color.*—New foliage: upper side—Acajou Red, Plate 13; under side—Varley's Green, Plate 18, lightly overcast with Garnet Brown, Plate 1. Old foliage: upper side—Dark Cress Green, Plate 31; under side—Cress Green, Plate 31.

*Shape.*—Oval pointed.

*Texture.*—Upper side—leathery; under side—rough.

*Ribs and veins.*—Ordinary.

*Edge.*—Serrated (saw-toothed).

*Serration.*—Both double and single; small.

*Leaf Stem.*—Color—Forest Green, Plate 17. Under side—smooth.

*Stipules.*—Medium length; smooth.

Wood:

*New wood.*—Color—Biscay Green, Plate 17. Bark—smooth.

*Old wood.*—Color—Dark Cress Green, Plate 31. Bark—smooth.

Thorns:

*Thorns.*—Quantity: on main stalks from base—few; on laterals from stalk—few. Form—short; straight; with narrow base. Color (when young)—Oxblood Red, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by its large, firm and stiff flower petals which are very resistant to rain, its strong flowering stems and stiff necks which always maintain the flowers facing upward, and the Buff Yellow, lightly overcast with Baryta Yellow, general color tonality of its flowers which lightens but does not fade completely even at the final stage of maturity.

No references cited